United States Patent
Wong et al.

(10) Patent No.: US 9,724,304 B2
(45) Date of Patent: Aug. 8, 2017

(54) NANOSPHERES FOR THERAPEUTIC AGENT DELIVERY

(71) Applicant: Temple University—Of The Commonwealth System of Higher Education, Philadelphia, PA (US)

(72) Inventors: Ho Lun Wong, Elkins Park, PA (US); Mayuri Narvekar, Philadelphia, PA (US); Hui Yi Xue, Elkins Park, PA (US)

(73) Assignee: TEMPLE UNIVERSITY—Of The Commonwealth System of Higher Education, Philadelphia, PA (US)

( * ) Notice: Subject to any disclaimer, the term of this patent is extended or adjusted under 35 U.S.C. 154(b) by 27 days.

(21) Appl. No.: 13/918,019

(22) Filed: Jun. 14, 2013

(65) Prior Publication Data

US 2013/0337077 A1    Dec. 19, 2013

Related U.S. Application Data

(60) Provisional application No. 61/659,658, filed on Jun. 14, 2012.

(51) Int. Cl.
| | | |
|---|---|---|
| *A61K 9/16* | (2006.01) | |
| *A61K 31/203* | (2006.01) | |
| *A61K 31/405* | (2006.01) | |
| *A61K 9/51* | (2006.01) | |

(52) U.S. Cl.
CPC .............. *A61K 9/16* (2013.01); *A61K 9/5123* (2013.01); *A61K 9/5153* (2013.01); *A61K 31/203* (2013.01); *A61K 31/405* (2013.01)

(58) Field of Classification Search
CPC ...... A61K 9/16; A61K 31/203; A61K 31/405; A61K 9/5123; A61K 9/5153
See application file for complete search history.

(56) References Cited

U.S. PATENT DOCUMENTS

| | | | |
|---|---|---|---|
| 3,971,852 A | | 7/1976 | Brenner et al. |
| 4,124,526 A | | 11/1978 | Allart et al. |
| 5,288,502 A | * | 2/1994 | McGinity et al. ............ 424/484 |
| 5,362,424 A | | 11/1994 | Lee et al. |
| 5,718,922 A | | 2/1998 | Herrero-Vanrell et al. |
| 5,916,597 A | | 6/1999 | Lee et al. |
| 6,001,895 A | | 12/1999 | Harvey et al. |
| 6,608,017 B1 | | 8/2003 | Dihora et al. |
| 2005/0170004 A1 | * | 8/2005 | Rosenberger et al. ....... 424/490 |
| 2006/0073203 A1 | * | 4/2006 | Ljusberg-Wahren ............... A61K 9/1075 424/469 |
| 2007/0087022 A1 | * | 4/2007 | Desai et al. ................... 424/400 |
| 2012/0141531 A1 | * | 6/2012 | Coulter et al. ............. 424/236.1 |

FOREIGN PATENT DOCUMENTS

| | | |
|---|---|---|
| WO | 2004/108884 | * 12/2004 |
| WO | 2004108884 | 12/2004 |
| WO | 2010133609 | 11/2010 |
| WO | 2011018504 | 2/2011 |

OTHER PUBLICATIONS

Jadhav et al ("Glass transition temperature: Basics and application in pharmaceutical sector," Asian J Pharm 2009;3:82-89).*
Table of Fatty Acids; Virtural Chembook, 2003; http://chemistry.elmhurst.edu/vchembook/551fattyacids.html.*
Makadia et al. Poly Lactic-co-Glycolic Acid (PLGA) as biodegradable controlled drug delivery carrier, Polymers, 2011, 3:1377-1397.
Pinto Reis et al. Nanoencapsulation I. Methods for preparation of drug-loaded polymeric nanoparticles, Nanomedicine, 2006, 2:8-21.
Narvekar et al., "Formulation and characterization of a novel polymer-oil nanostructured carrier for sustained release and efficient encapsulation of highly lipophilic drugs", Oct. 24, 2011, M1024 Abstract Presented at 2011 AAPS Annual Meeting and Expo.
Narvekar et al., "Evaluation of in vitro toxicity of a novel polymer-oil nanostructured carrier in human prostate and breast cell models", Oct. 24, 2011, M1025 Abstract Presented at 2011 AAPS Annual Meeting and Expo.

* cited by examiner

*Primary Examiner* — Suzanne Ziska
(74) *Attorney, Agent, or Firm* — Drinker Biddle & Reath LLP

(57) ABSTRACT

Provided is a nanosphere for delivery of a therapeutic agent comprising: a polymer matrix; discrete liquid oil droplets dispersed in the polymer matrix; and a therapeutic agent dissolved or dispersed in the oil. In some embodiments, the nanosphere is pegylated. In some embodiments, the nanosphere has a diameter of from about 100 nm to about 300 nm. In further preferred embodiments, the nanosphere has a diameter of from about 150 nm to about 250 nm. In yet further embodiments, the nanosphere has a diameter of from about 180 nm to about 220 nm. In some embodiments, the oil comprises a lipid or a phospholipid. In further embodiments, the lipid or the phospholipid has a melting point below 20° C. In some embodiments, the polymer is a natural, modified or synthetic polymer. In further embodiments, the polymer is biodegradable.

29 Claims, 15 Drawing Sheets

Polymer matrix

Drug particles present on the surface

Polymer matrix

Lipid pockets containing drug

Yellowish-green fraction containing unencapsulated ATRA drug solid (partially washable)

Nearly colorless fraction of PLGA-np (not washable)

Homogeneous fraction of PONC (not washable)

Figure 5B

| | ATRA released (%) | |
|---|---|---|
| | 30 min | 24 h |
| PLGA-np | 69.09 ± 5.19 | 93.4 ± 2.44 |
| PONC | 7.89 ± 7.66 | 72.24 ± 2.87 |

NANOSPHERES FOR THERAPEUTIC AGENT DELIVERY

CROSS-REFERENCE TO RELATED APPLICATION

The benefit of the filing date of U.S. Provisional Patent Application No. 61/659,658, filed Jun. 14, 2012, is hereby claimed. The entire disclosure of the aforesaid application is incorporated herein by reference.

FIELD OF THE INVENTION

The invention relates to nanospheres for therapeutic agent delivery.

BACKGROUND OF THE INVENTION

Biocompatible, biodegradable colloidal systems for drug delivery are commonly made of either lipids or polymers (Balmayor et al., 2011, Controlled delivery systems: from pharmaceuticals to cells and genes. *Pharm Res* 28, 1241-1258; Bunjes, 2010, Lipid nanoparticles for the delivery of poorly water-soluble drugs. *J of Pharmacy and Pharmacology* 62, 1637-1645; Wong et al., 2010, Nanotechnology applications for improved delivery of antiretroviral drugs to the brain. *Advanced Drug Delivery Reviews* 62, 503-517). Both materials have their own advantages. While lipid colloids are inherently more efficient systems for encapsulation of the highly lipophilic compounds, and are less likely to cause toxic or immunogenic responses (Müller et al., 2000, Solid lipid nanoparticles (SLN) and nanostructured lipid carriers (NLC) in cosmetic and dermatological preparations, *Adv Drug Deliv Rev* 54 Suppl 1, S131-155; Salvador-Morales et al., 2009, Immunocompatibility properties of lipid-polymer hybrid nanoparticles with heterogeneous surface functional groups. *Biomaterials* 30, 2231-2240), on comparative terms, polymeric colloids (e.g. polymeric nanoparticles) can be easily fabricated at low temperature, are able to deliver both hydrophilic and lipophilic drugs, and have uniform and reproducible size distribution and morphology (Barratt, 2003, Colloidal drug carriers: achievements and perspectives. *Cell Mol Life Sci* 60, 21-37; Panyam and Labhasetwar, 2003, Biodegradable nanoparticles for drug and gene delivery to cells and tissue. *Adv Drug Deliv Rev* 55, 329-347). Because newer drugs tend to have high lipophilicity and these drugs often have delivery issues (Cai et al., 2010, Nanocarriers: a general strategy for enhancement of oral bioavailability of poorly absorbed or pre-systemically metabolized drugs. *Curr Drug Metab* 11, 197-207), the need for lipid-based systems with an improved design, possibly incorporating some advantages of polymeric systems, has become particularly strong.

Colloids made of solid lipids (e.g. solid lipid nanoparticles) and oil droplets (e.g. nanoemulsion) have been extensively studied for lipophilic delivery in recent years with promising results. However, solid lipid nanoparticles tend to slowly release their entrapped drugs for weeks, which may be unsuitable for many non-chronic disease conditions (Wong et al., 2007, Chemotherapy with anticancer drugs encapsulated in solid lipid nanoparticles. *Advanced Drug Delivery Reviews* 59, 491-504), whereas nanoemulsions made of fine oil droplets may encounter stability issues like Ostwald ripening as well as technical issues such as difficulty to lyophilize (Li et al., 2009, PEG-PLA diblock copolymer micelle-like nanoparticles as all-trans-retinoic acid carrier: in vitro and in vivo characterizations. *Nanotechnology* 20, 055106; Tadros et al., 2004, Formation and stability of nano-emulsions. *Advances in Colloid and Interface Science* 108-109, 303-318). Researchers are still searching for a closer-to-ideal nanocarrier, especially for the controlled delivery of lipophilic; poorly water-soluble compounds.

"Hybrid" nanotechnology has been previously developed, in which polymers are embedded into nanoparticle cores of mostly solid lipids and/or phospholipids. The polymer component enables efficient binding of hydrophilic compounds and the lipid matrix serves to control their release (Wong et al., 2006, A new polymer-lipid hybrid nanoparticle system increases cytotoxicity of doxorubicin against multidrug-resistant human breast cancer cells. *Pharm Res* 23, 1574-1585). The combination of the advantages of both polymers and lipids in a single nanocarrier has made this design attractive to others as well (Liu et al., 2010, Folic acid conjugated nanoparticles of mixed lipid monolayer shell and biodegradable polymer core for targeted delivery of Docetaxel. *Biomaterials* 31, 330-338; Zhang et al., 2008, All-trans retinoic acid (atRA) differentially induces apoptosis in matched primary and metastatic melanoma cells—a speculation on damage effect of at RA via mitochondrial dysfunction and cell cycle redistribution. *Carcinogenesis* 24, 185-191).

A disadvantage of drug-loaded solid lipid nanoparticles is that the solid materials tend to pack tightly and contract during solidification. This process often drives the loaded drug molecules towards the solid nanoparticle surface to increase the risk of uncontrolled initial drug releases (Wong et al., 2007, Chemotherapy with anticancer drugs encapsulated in solid lipid nanoparticles. *Advanced Drug Delivery Reviews* 59, 491-504). Inclusion of oil into solid lipids was found to introduce internal room or "nanostructure" within the particle cores by increasing their amorphosity, leading to more uniform drug distribution and improved drug release profiles (Muller et al., 2002, Solid lipid nanoparticles (SLN) and nanostructured lipid carriers (NLC) in cosmetic and dermatological preparations. *Adv Drug Deliv Rev* 54 Suppl 1, S131-155).

PLGA copolymers belong to one of the very few classes of biomaterials widely approved for biomedical applications (Bala et al., 2004, PLGA nanoparticles in drug delivery: the state of the art. *Crit Rev Ther Drug Carrier Syst* 21, 387-422), (Astete and Sabliov, 2006, Synthesis and characterization of PLGA nanoparticles. *J of Biomaterials Science, Polymer Edition* 17, 247-289). Polymeric drug carriers build with PLGA are highly biocompatible and biodegradable, possess uniform and reproducible size and morphology, and have good storage and handling properties (Astete and Sabliov, 2006, Synthesis and characterization of PLGA nanoparticles. *J of Biomaterials Science, Polymer Edition* 17, 247-289).

There remains a need for a nanocarrier for the controlled delivery of lipophilic, poorly water-soluble compounds.

SUMMARY OF THE INVENTION

Provided is a nanosphere for delivery of a therapeutic agent comprising:
a polymer matrix;
discrete liquid oil droplets dispersed in the polymer matrix; and
a therapeutic agent dissolved or dispersed in the oil droplets.

In some embodiments, the nanosphere is pegylated.

In some embodiments, the nanosphere has a diameter of from about 100 nm to about 300 nm. In further preferred embodiments, the nanosphere has a diameter of from about 150 nm to about 250 nm. In yet further embodiments, the nanosphere has a diameter of from about 180 nm to about 220 nm. In some embodiments, the oil comprises a lipid or a phospholipid. In further embodiments the oil is selected from the group consisting of palmitoleic acid, oleic acid, linoleic acid, α-linoleic acid, arachidonic acid, propylene glycol monocaprylate, propylene glycol dicaprylate, propylene glycol dicaprate, glycerol monocaprate and glycerol monooleate. In yet further embodiments, the lipid or the phospholipid has a melting point below 20° C. In some embodiments, the polymer is a natural, modified or synthetic polymer. In further embodiments, the polymer is biodegradable. In yet further embodiments the polymer is selected from the group consisting of a polylactic acid polymer, a polyglycolic acid polymer, a poly(lactic-co-glycolic acid) copolymer, an acrylic polymer, a polyhydroxyalkanoate polymer, a polyethylenimine, an acrylamide polymer and a chitosan polymer.

In some embodiments, the discrete liquid oil droplets are evenly dissolved or dispersed in the polymer matrix. In further embodiments, the nanospheres provide a uniform rate of release. In yet further embodiments, differential scanning calorimetry (DSC) of the nanospheres yields a single peak. In some embodiments, the ratio of polymer:oil is from about 70:30 to about 90:10. In preferred embodiments, the ratio of polymer:oil is from about 70:30 to about 80:20. In further preferred embodiments, the ratio of polymer:oil is from about 75:25 to about 78:22.

In some embodiments, the therapeutic agent is a poorly water soluble drug. In further embodiments the poorly water soluble drug is an antineoplastic agent, a steroidal hormone, a sex hormone, an anti-fungal drug, an anti-viral drug, an antibiotic, an opioid agonist, an opioid antagonist, a calcium channel blocker, an antiangiogenic drug, a diagnostic compound, a vitamin or a cosmetic compound.

In some embodiments, the therapeutic agent is interferon, macrophage activation factor, an interleukin, colony stimulating factor, tumor degenerating factor, epidermal growth factor, erythropoietin, tissue plasminogen activator, insulin, luteinizing hormone releasing hormone, an enzyme, a vaccine or an antibody. In further embodiments, the enzyme is urokinase or superoxide dismutase.

In some preferred embodiments, the nanosphere is prepared by emulsion-solvent evaporation of a solvent for said polymer.

Provided is a method for preparing a nanosphere comprising the steps of:

dissolving a therapeutic agent in an oil;

adding a solvent for the therapeutic agent and the oil to form a solution;

adding a polymer to said solution with mixing to form a mixture;

adding said mixture to a solvent for the polymer with mixing; and evaporating the solvent for the polymer to obtain a nanosphere comprising the therapeutic agent dissolved or dispersed in oil droplets dispersed in a matrix formed by said polymer. In some preferred embodiments, the solvent for the therapeutic agent and the oil is dichloromethane. In further preferred embodiments, the solvent for the polymer is an alcohol. In yet further preferred embodiments, the solvent for the polymer is an aqueous solution of an alcohol.

In some embodiments, the nanosphere has a diameter of from about 100 nm to about 300 nm. In further preferred embodiments, the nanosphere has a diameter of from about 150 nm to about 250 nm. In yet further embodiments, the nanosphere has a diameter of from about 180 nm to about 220 nm. In some embodiments, the oil comprises a lipid or a phospholipid. In further embodiments the oil is selected from the group consisting of palmitoleic acid, oleic acid, linoleic acid, α-linoleic acid, arachidonic acid, propylene glycol monocaprylate, propylene glycol dicaprylate, propylene glycol dicaprate, glycerol monocaprate and glycerol monooleate. In yet further embodiments, the lipid or the phospholipid has a melting point below 20° C. In some embodiments, the polymer is a natural, modified or synthetic polymer. In further embodiments, the polymer is biodegradable. In yet further embodiments the polymer is selected from the group consisting of a polylactic acid polymer, a polyglycolic acid polymer, a poly(lactic-co-glycolic acid) copolymer, an acrylic polymer, a polyhydroxyalkanoate polymer, a polyethylenimine, an acrylamide polymer and a chitosan polymer.

In some embodiments, the discrete liquid oil droplets are evenly dissolved or dispersed in the polymer matrix. In further embodiments, the nanospheres provide a uniform rate of release. In yet further embodiments, differential scanning calorimetry (DSC) of the nanospheres yields a single peak. In some embodiments, the ratio of polymer:oil is from about 70:30 to about 90:10. In preferred embodiments, the ratio of polymer:oil is from about 70:30 to about 80:20. In further preferred embodiments, the ratio of polymer:oil is from about 75:25 to about 78:22.

In some embodiments, the therapeutic agent is a poorly water soluble drug. In further embodiments the poorly water soluble drug is an antineoplastic agent, a steroidal hormone, a sex hormone, an anti-fungal drug, an anti-viral drug, an antibiotic, an opioid agonist, an opioid antagonist, a calcium channel blocker, an antiangiogenic drug, a diagnostic compound, a vitamin or a cosmetic compound.

In some embodiments, the therapeutic agent is interferon, macrophage activation factor, an interleukin, colony stimulating factor, tumor degenerating factor, epidermal growth factor, erythropoietin, tissue plasminogen activator, insulin, luteinizing hormone releasing hormone, an enzyme, a vaccine or an antibody. In further embodiments, the enzyme is urokinase or superoxide dismutase.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

BRIEF DESCRIPTION OF THE DRAWINGS

FIG. 5B is a table highlighting the beginning and end point values obtained. Data is represented as means±S.D. (N=3).

FIG. 6A illustrates the average particle diameter as measured with photon correlation spectroscopy. Data is represented as means±S.D. (N=3). The mini-table in FIG. 6A presents the particle size before or after freeze-drying (FD). FIG. 6B illustrates the polydispersity index of particle size. FIG. 6C illustrates zeta potential values. Data is represented as means±S.D. (N=3). FIG. 6D represents differential scanning calorimetry (DSC) thermograms of PONC nanospheres at the beginning (A, day 1) and end of storage (B, 7 days at room temperature; C, 14 days at 4° C.; D, −20° C.).

DEFINITIONS

Figure 1A:
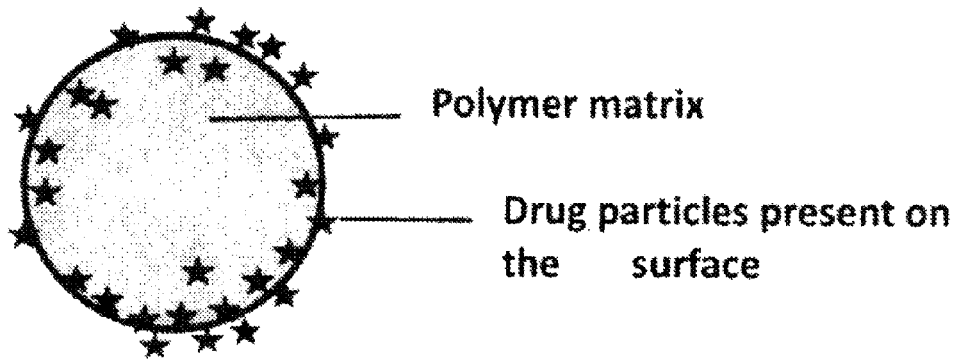
FIG. 1A illustrates conventional PLGA only nanoparticles (PLGA-np).

As used herein, each of the following terms has the meaning associated with it in this section.

The articles "a" and "an" are used herein to refer to one or to more than one (i.e. to at least one) of the grammatical object of the article. By way of example, "an element" means one element or more than one elements.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

The term "polymer matrix," as used herein, describes a three-dimensional solid comprising a polymer.

The term "dispersed," as used herein, describes being distributed or spread out over an area. The term "evenly dispersed," as used herein, describes being distributed or spread out over an area in roughly equal amounts.

The term "therapeutic agent," as used herein, describes a drug or a polypeptide for use in the treatment of a disease or medical condition. In some embodiments, the drug is a water soluble drug. In some preferred embodiments, the drug is a poorly water soluble drug. In further preferred embodiments, the poorly water soluble drug is an antineoplastic agent, a steroidal hormone, a sex hormone, an anti-fungal drug, an anti-viral drug, an antibiotic, an opioid agonist, an opioid antagonist, a calcium channel blocker, an antiangiogenic drug, a diagnostic compound, a vitamin or a cosmetic compound. In some preferred embodiments, the polypeptide is interferon, macrophage activation factor, an interleukin, colony stimulating factor, tumor degenerating factor, epidermal growth factor, erythropoietin, tissue plasminogen activator, insulin, luteinizing hormone releasing hormone, an enzyme, a vaccine or an antibody. In further preferred embodiments, the enzyme is urokinase or superoxide dismutase.

The term "nanoparticle," as used herein, describes a particle with a diameter from about 1 nm to about 300 nm. As used herein, "particle size" and "particle diameter" have the same meaning.

The term "poor water solubility," as used herein, describes compounds including those that are considered "slightly soluble" (100 to 1000 parts solvent needed to dissolve 1 part solute), "very slightly soluble" (1000 to 10,000 parts solvent needed to dissolve 1 part solute), and "practically insoluble" (more than 10,000 parts solvent needed to dissolve 1 part solute), according to the United States Pharmacopeia (USP).

The term "uniform rate of release," as used herein, describes the lack of significant burst release of drug from the carrier device, i.e. less than 20% drug release in the first hour, less than 40% drug release in the first 4 hours, and less than 80% drug release in the first 24 hours.

The term "emulsion-solvent evaporation," as used herein, describes a process for preparing the nanospheres disclosed herein. A therapeutic agent is dissolved in oil, and the resulting drug-oil phase is diluted with a solvent. In this solution a polymer is dispersed. The resulting organic phase is slowly added to a solvent for the polymer. The resulting mixture is further mixed. The solvent for the polymer is then evaporated. In some preferred embodiments, the solvent for the polymer is an alcohol.

DETAILED DESCRIPTION OF THE INVENTION

Provided are hybrid nanospheres comprising a therapeutic agent dissolved or dispersed in oil droplets dispersed in a matrix formed by a polymer.

Nanospheres for Delivery of a Therapeutic Agent

Figure 1B:
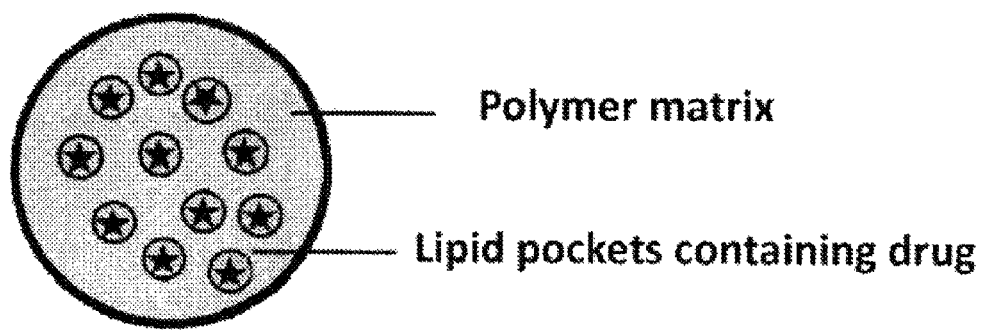
FIG. 1B illustrates the polymer-oil hybrid nanosphere carrier (PONC) system.

Disclosed herein is the integration of oil into a polymer matrix to form a polymer-oil hybrid nanosphere carrier (PONC) for delivery of a therapeutic agent. A schematic illustration of the nanosphere is shown in FIG. 1B. The figures illustrate the key difference between conventional PLGA nanoparticles (PLGA-np; FIG. 1A) and the PONC (FIG. 1B). The figures also highlight the rationale behind the higher encapsulation efficiency for the PONC. The PONC are prepared by dispersing liquid oil droplets in a polymeric matrix, e.g., a polymer matrix of poly(d,l-lactic-co-glycolic acid) (PLGA).

Several advantages are achieved with this PONC design. The incorporation of oil in the polymer matrix enables efficient encapsulation of lipophilic, poorly water-soluble drugs in a dissolved or dispersed state. Meanwhile, the use of biodegradable, biocompatible polymers provides an easily fabricable nanocarrier framework stabilizing the oil/drug components and allowing lyophilization of the resulting particles.

The nanosphere-based delivery system disclosed herein confers the key strength of lipid-based drug carriers, i.e. efficient encapsulation of lipophilic compounds, to a polymer matrix system without distracting from the useful qualities of the polymer matrix system. As shown in the examples below, the nanosphere-based system disclosed herein provides benefits such as improved size uniformity and improved release kinetics. The rate of release of the therapeutic agent is more uniform in the presently provided nanospheres than in PLGA-np or in microspheres. This presents a significant advantage over previously known delivery methods. DSC of the nanospheres provided herein results in a single peak. DSC of microspheres of similar composition results in two peaks, where one peak corresponds to the oil phase and one peak corresponds to the polymer phase.

Another important advantage of the presently provided nanospheres is that their small size permits intravenous and intraarterial injection. This is not possible with larger particles such as microspheres or microparticles. The nanospheres described herein can be functionalized to target specific tissues. They also can be pegylated, to prevent degradation of the nanospheres by the immune system.

Figure 2A:
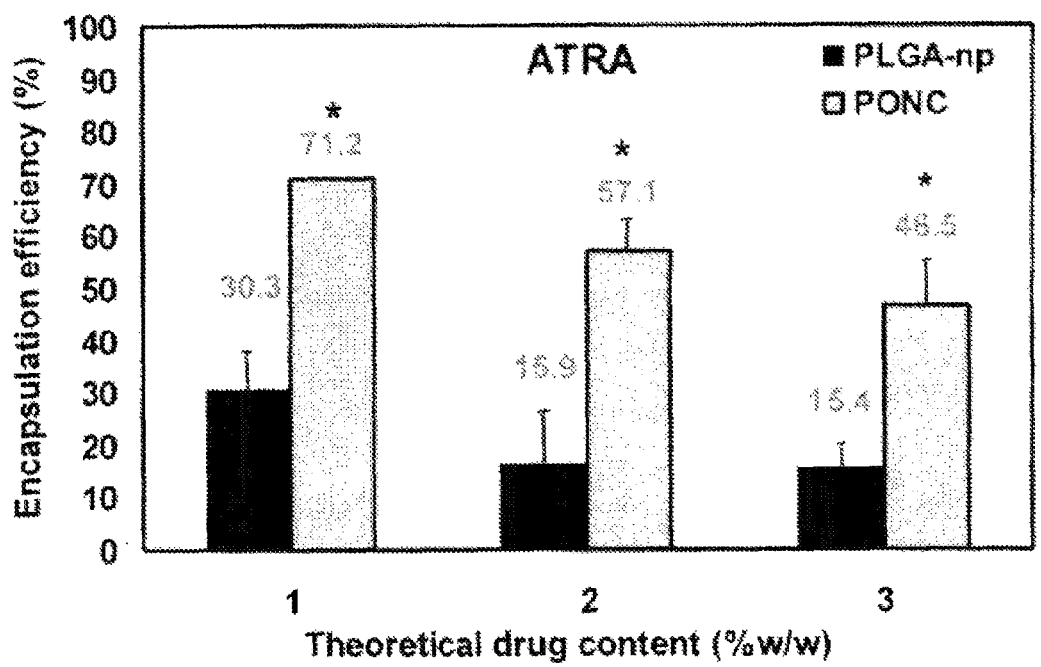
FIG. 2A compares the encapsulation efficiency (%) of PLGA-np and the PONC at different targeted loadings of all-trans retinoic acid (ATRA).
Figure 2B:
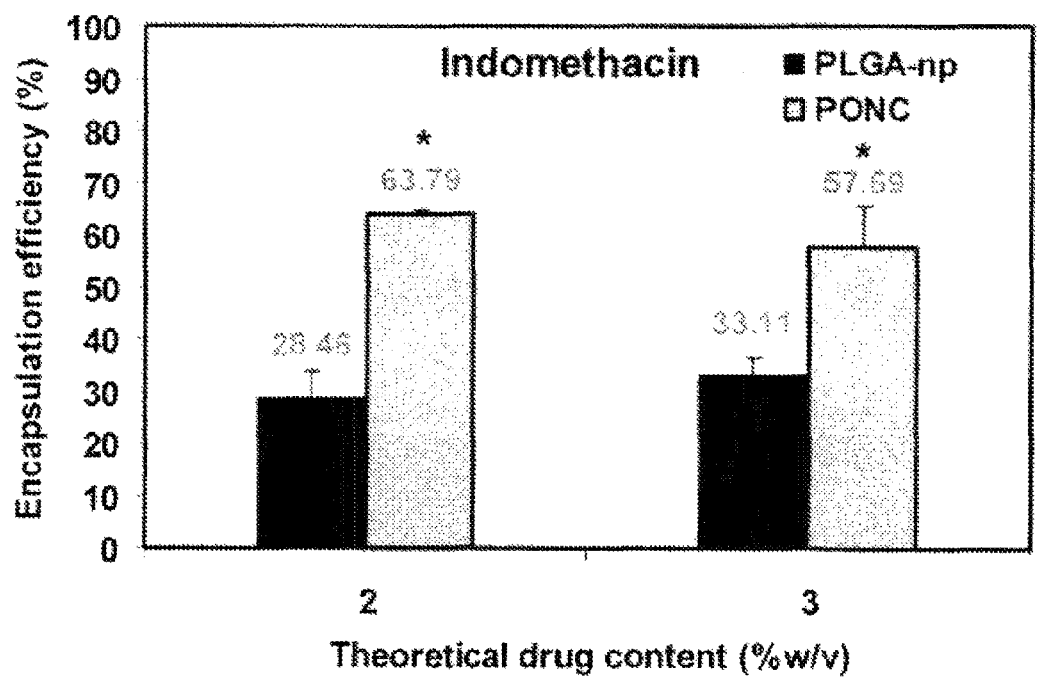
FIG. 2B compares the encapsulation efficiency (%) of PLGA-np and the PONC nanospheres at different targeted loadings of indomethacin. *$p<0.05$ comparing PLGA-np and the PONC nanospheres. The numbers above the bars in the graph indicate the numeric values.

Poorly water-soluble drugs tend to precipitate out in the continuous phase during formulation of the oil-in-water emulsions (Calvo et al., 1996, Comparative in vitro evaluation of several colloidal systems, nanoparticles, Nanocapsules, and nanoemulsions, as ocular drug carriers. *J Pharm Sci* 85, 530-536). For highly lipophilic drugs such as ATRA and indomethacin (IDMC), this phenomenon significantly compromises their encapsulation using conventional polymeric nanosystems. According to the present invention, highly lipophilic therapeutic agents are encapsulated in nanosphere systems by taking advantage of these agents' compatibility with oil. This advantage is particularly significant at higher targeted drug loading (e.g. 2 or 3%) of extremely lipophilic compounds such as ATRA. As shown in FIG. 2A, a 200% increase in encapsulation efficiency was achieved by the nanospheres of the invention over standard PLGA-np. This advantage persisted when ATRA was replaced with a less lipophilic compound, IDMC. A 124% increase in encapsulation efficiency ($p<0.05$) was observed when 2% IDMC-loaded nanospheres of the invention were compared to PLGA-np (FIG. 2B).

Many drug compounds, especially for cancer and HIV treatments, are moderately to highly lipophilic. Their uses are frequently limited by their poor aqueous solubility (Lu et al., 2007, Mesoporous Silica Nanoparticles for Cancer Therapy: Energy-Dependent Cellular Uptake and Delivery of Paclitaxel to Cancer Cells. *Nanobiotechnology* 3, 89-95; Aungst, 1999, P-glycoprotein, secretory transport, and other barriers to the oral delivery of anti-HIV drugs. *Advanced Drug Delivery Reviews* 39, 105-116). The hybrid nanospheres and administration system of the present invention provide for the efficient encapsulation of highly lipophilic drugs at relatively high drug loadings.

Therapeutic Agents that May be Delivered by the Presently Provided Nanospheres

Therapeutic agents are dispersed or dissolved in the oil droplets that are dispersed in the polymer of the nanosphere. Therapeutic agents that are either water soluble or poorly water soluble may be delivered by the presently provided nanospheres. The poorly water soluble therapeutic agent may be, for example, an antineoplastic agent, steroidal hormone, sex hormone, anti-fungal drug, anti-viral drug, antibiotic, opioid agonist, opioid antagonist, calcium channel blocker, antiangiogenic drug, diagnostic compound, cosmetic compound, peptide or vaccine.

The antineoplastic agent may comprise, for example, a differentiating agent, a plant alkaloid or its derivatives, a topoisomerase inhibitor, an anticancer antibiotic or an antimetabolite. In preferred embodiments the differentiating agent is all-trans retinoic acid. In preferred embodiments, the plant alkaloid or plant alkaloid derivative is paclitaxel, docetaxel, etoposide, camptothecin, vinblastine, vincristine, vindesine, vinorelbine or vinoreline. In preferred embodiments, the topoisomerase inhibitor is topotecan or irinotecan. In preferred embodiments the aromatase inhibitor is anastrozole or letrozole. In further preferred embodiments, the anticancer antibiotic is doxorubicin, daunorubicin, valrubicin, bleomycin, dactinomycin, epirubicin, idarubicin, mitoxantrone or mitomycin. In yet further preferred embodiments, the antimetabolite is methotrexate, pemetrexed, raltitrexed, cladribine, clofarabine, fludarabine, mercaptopurine, fluorouracil or gemcitabine.

Hormone antagonists that may be delivered by the presently provided nanospheres comprise antiestrogens, gonadotropin-releasing hormone (GnRH) antagonists and leutinizing hormone releasing hormone (LHRH) antagonists, for example. In preferred embodiments the antiestrogen is raloxifen or tamoxifen. In further preferred embodiments, the GnRH antagonist is cetrorelix or ganirelix. In yet further preferred embodiments, the LHRH antagonist is leuprolide or goserelin.

Steroidal hormones that may be delivered by the presently provided nanospheres comprise, for example, anabolic steroids, corticosteroidal hormones, physiologically equivalent hormone derivatives or combinations thereof. In preferred embodiments, the anabolic steroid is androstenolone, androstenone, nandrolol, nerobolil or retabolil. In further preferred embodiments, the corticosteroidal hormone is betamethasone, dexamethasone, hydrocortisone, progesterone, prednisolone or a fluorinated corticosteroid.

Sex hormones that may be delivered by the presently provided nanospheres comprise, for example, androgens and estrogens. In preferred embodiments, the androgen is testosterone or dihydrotestosterone. In further preferred embodiments, the estrogen is estradiol or norestradiol.

Antiviral agents that may be delivered by the presently provided nanospheres comprise, for example, entry inhibitors, protease inhibitors, integrase inhibitors, maturation inhibitors and CCR5 receptor agonists. In preferred embodiments, the entry inhibitor is maraviroc or enfuvirtide. In further preferred embodiments, the protease inhibitor is saquinavir, ritonavir, indinavir, nelfinavir, amprenavir, lopinavir, atazanavir, fosamprenavir, tipranavir or darunavir. In yet further preferred embodiments, the integrase inhibitor is elvitegravir or raltegravir. In preferred embodiments, the maturation inhibitor is bevirimat. In further preferred embodiments, the CCR5 receptor agonist is aplaviroc or vicriviroc.

Antibiotics that may be delivered by the presently provided nanospheres comprise, for example, aminoglycosides, fluoroquinolones, macrolides, rifampines or tetracyclines. In preferred embodiments, the aminoglycoside is gentamycin, tobramycin, streptomycin or amikacin. In further preferred embodiments, the fluoroquinolone is ciproflaxin, moxifloxacin or gatifloxacin. In yet further preferred embodiments, the macrolide is azithromycin or clarithromycin. In preferred embodiments, the rifampine is rifampicin or rifabutine. In further preferred embodiments, the tetracycline is doxycyclin or minocyclin.

Other therapeutic agents that may be delivered by the presently provided nanospheres comprise, for example, skin whitening agents, sunscreen ingredients and oil-soluble vitamins. In preferred embodiments, the skin whitening ingredient is hydroquinone or monobenzone. In further preferred embodiments, the sunscreen ingredient is avobenzone bemotrizinol, octocrylene, padimate 0, octyl salicylate or octyl methoxycinnamate. In yet further preferred embodiments, the oil-soluble vitamin is vitamin D or derivatives thereof, or vitamin E or derivatives thereof.

Polymers

The matrix portion of the presently provided nanospheres may comprise natural, modified or synthetic polymers. In some embodiments, the nanospheres may comprise polylactic acid polymers, polyglycolic acid polymers, the copolymer poly(lactic-co-glycolic acid), and derivatives thereof. In further embodiments, the nanospheres may comprise acrylic polymers, including poly(butyl cyanate), poly(propyl cyanate) and derivatives thereof. In yet further embodiments, the nanospheres may comprise polyhydroxyalkanoate and derivatives thereof. In preferred embodiments, the polyhudroxyalkanoate is polyhydroxybutyrate, polyhydroxyvalerate or polyhydroxyoctanoate. In some embodiments, the nanospheres may comprise polyethylenimine or derivatives thereof. In further embodiments, the nanospheres may comprise acrylamide based polymers or derivatives thereof. In preferred embodiments, the acrylamide based polymer is poly(N-isopropyl acrylamide). In some embodiments, the nanospheres may comprise chitosans or derivatives thereof.

Oils

The oil droplets dispersed in the polymer matrix of the nanospheres may comprise, for example, lipids or phospholipids with melting points below 20° C. In some embodiments, the oil may comprise monounsaturated fatty acids or polyunsaturated fatty acids. In preferred embodiments, the monounsaturated fatty acid or polyunsaturated fatty acid is palmitoleic acid, oleic acid, linoleic acid, α-linolenic acid or arachidonic acid. In some embodiments, the oil may comprise propylene glycol mono- and diesters of saturated fatty acids or propylene glycol mono- and diesters of unsaturated fatty acids. In preferred embodiments, the propylene glycol mono- or diester of saturated fatty acids or propylene glycol mono- or diester of unsaturated fatty acids is propylene glycol monocaprylate, propylene glycol dicaprylate or propylene glycol dicaprate. In further embodiments, the oil may comprise mono-diglyceride medium chain esters of saturated and unsaturated fatty acids. In preferred embodiments, the mono-diglyceride medium chain esters of saturated or unsaturated fatty acid is glyceryl monocaprate or glyceryl monooleate.

The invention should not be construed to be limited solely to the compositions and methods described herein, but should be construed to include other compositions and methods as well. One of skill in the art will know that other compositions and methods are available to perform the procedures described herein.

Nanosphere Preparation

The presently provided nanospheres are prepared by emulsion-solvent evaporation technique. The therapeutic agent is dissolved or dispersed in oil. In some preferred embodiments, the oil is a propylene glycol ester, such as an ester of caprylic and/or capric acid. In some embodiments, the oil comprises mixed diesters of caprylic acid/capric acids of propylene glycol, e.g. Captex 200 (ABITEC Corp., Janesville, Wis.). In further preferred embodiments, the therapeutic agent is dissolved or dispersed in oil by incubating at room temperature overnight. The resulting drug-oil phase is diluted with a solvent for the drug and the oil. In some embodiments, the solvent is dichloromethane, chloroform, diethyl ether, n-pentane, cyclopentane, h-hexane, tetrahydrofuran and mixtures thereof. In preferred embodiments, the solvent is dichloromethane. In further preferred embodiments, the solvent for the drug and the oil is capable of dissolving polymer. To this solution polymer is dispersed. In preferred embodiments, the polymer is PLGA. The amount of oil may be varied depending on the nanosphere formulation desired. In preferred embodiments, the amount of oil varies from about 3 mg to about 9 mg. Thus, in preferred embodiments, the range of polymer:oil ratio in the nanospheres may vary from about 70:30 to about 90:10. In preferred embodiments, the ratio of polymer:oil is from about 70:30 to about 80:20. In further preferred embodiments, the ratio of polymer:oil is from about 75:25 to about 78:22. The resulting organic phase is added to a solvent for the polymer with mixing. In some preferred embodiments, the solvent for the polymer is an alcohol. In some preferred embodiments, the solvent for the polymer is an aqueous solution of an alcohol. In further preferred embodiments, the alcohol is a $C_1$-$C_6$ alcohol. In some embodiments, the solvent for the polymer is acetone. The emulsion formed is stirred for solvent evaporation. In preferred embodiments, the nanospheres formed may be freshly used or lyophilized.

The same procedure may be used for the preparation of polymer-only nanoparticles (i.e. PLGA-np), for purposes of comparison, except that oil is not included.

The practice of the invention is illustrated by the following non-limiting examples.

EXAMPLES

In the following Examples, the results are expressed as mean±Standard Deviation. The significance of differences was assessed using Student's t-test and $p<0.05$ was considered significant unless otherwise specified.

Model Drugs

Two model drugs were selected for encapsulation in the studies described in the following Examples. All-trans retinoic acid (ATRA) was used as the primary model compound because of its high lipophilicity and extremely low water-solubility (aqueous solubility=0.029 mg/ml at 25° C.) (Chinsriwongkul et al., 2007, Physicochemical properties of lipid emulsions formulated with high-load all-trans-retinoic acid. *PDA J Pharm Sci Technol* 61, 461-471), and the relatively less lipophilic indomethacin (IDMC) (aqueous solubility=0.035 mg/ml at 25° C.) (Nandi et al., 2003, Study of isopropyl myristate microemulsion systems containing cyclodextrins to improve the solubility of 2 model hydrophobic drugs. *AAPS PharmSciTech* 4, E10) served as a second drug for comparison. ATRA has been shown to be a promising anti-cancer agent (Hong et al., 2011, Combination of paclitaxel- and retinoic acid incorporated nanoparticles for the treatment of CT-26 colon carcinoma. *Arch Pharm Res* 34, 407-417; Okuno et al., 2004, Retinoids in cancer chemoprevention. *Curr Cancer Drug Targets* 4, 285-298; Ravandi, 2011, Acute promyelocytic leukemia can be treated successfully without cytotoxic chemotherapy. *Oncology (Williston Park)* 25, 741-743). Its clinical application, however, is limited by its poor water solubility, retinoid acute resistance, and the lack of an efficient delivery strategy (Li et al., 2009, PEG-PLA diblock copolymer micelle-like nanoparticles as all-trans-retinoic acid carrier: in vitro and in vivo characterizations. *Nanotechnology* 20, 055106; Park et al., 2008, Antitumor effect of all-trans retinoic acid-encapsulated nanoparticles of methoxy poly (ethylene glycol)-conjugated chitosan against CT-26 colon carcinoma in vitro. *J Pharm Sci* 97, 4011-4019). Successful encapsulation of ATRA was reportedly difficult because of its poor aqueous solubility and high lipophilicity (Chinsriwongkul et al., 2010, Oleic Acid enhances all-trans retinoic acid loading in nano-lipid emulsions. *PDA J Pharm Sci Technol* 64, 113-123). Previous attempts to encapsulate ATRA in liposomes had not been very fruitful because of low encapsulation efficiency and instability (Chinsriwongkul et al., 2007, Physicochemical properties of lipid emulsions formulated with high-load all-trans-retinoic acid. *PDA J Pharm Sci Technol* 61, 461-471). These issues are addressed by encapsulation in the hybrid nanospheres, with the oil component solubilizing the ATRA for efficient encapsulation and the polymeric matrix provides improved physical stability over lipid emulsion particles.

Example 1. Size of the Nanospheres and Zeta Potential Measurements

Chemicals and Reagents

PLGA 50:50 (viscosity 0.4 dl/g, molecular weight 44 kDa) and Captex 200 (i.e. propylene glycol dicaprylate/dicaprate) were kindly donated from Purac (Gorinchem, Netherlands) and Abitec (Janesville, Wis.), respectively. Indomethacin was purchased from Alfa Aesar, Spectra/Por dialysis membrane from spectrum (MWCO=10 kDa, Gardena, Calif., USA), dimethyl sulfoxide from Fisher Scientific (Pittsburgh, Pa., USA) and polyvinyl alcohol (PVA, molecular weight 30-70 kDa, 87-90% hydrolyzed), ATRA, dichloromethane and other chemicals were purchased from Sigma Aldrich, Inc. (St. Louis, Mo., USA).

Cell Cultures

The human prostate cancer PC-3 cell line and the immortalized human prostate RWPE-1 epithelial cell line were purchased from American Type Culture Collection (Manassas, Va.). PC-3 cells were grown in RPMI-1640 medium supplemented with 10% fetal bovine serum, 50,000 units penicillin G and 50,000 µg streptomycin. RWPE-1 cells were maintained in keratinocyte serum free medium (Invitrogen/GIBCO, Grand Island, N.Y.). The cells were maintained at 37° C. in humidified atmosphere of 5% $CO_2$. Cells used for experiments were from $10^{th}$ to $25^{th}$ passages.

Nanosphere Preparation

Nanospheres were prepared by emulsion-solvent evaporation technique. A model drug (ATRA or indomethacin) was dissolved in oil (Captex 200) by incubating at room temperature overnight, and the resulting drug-oil phase was diluted with 1 ml dichloromethane. To this solution 30 mg PLGA polymer was dispersed. Depending on the nanosphere formulation desired, the amount of oil used varied from 3 mg to 9 mg, so the range of PLGA: oil ratio in the nanospheres was from 90:10 to 70:30. The resulting organic phase was slowly added to 5 ml 1.5% aqueous solution of polyvinyl alcohol over a period of 2 min under constant stirring. The mixture was slightly vortexed for 10-15 seconds. The mixture was sonicated for 6 min on ice (40 kHz, 120 V, Bransonic 3510, Danbury Conn.). The emulsion formed was stirred overnight for solvent evaporation. The nanocarriers formed were freshly used or lyophilized for experiments. The same procedure was used for the preparation of standard PLGA-only nanoparticles (i.e. PLGA-np) except that oil was not included.

Size Distribution and Zeta Potentials

Particle size and zeta potential values were measured by photon correlation spectroscopy using Malvern Zetasizer NanoZS90 (Worcestershire, UK). Nanosphere or PLGA-np fresh samples were suspended in distilled water and 15 successive cycles were run at 25° C. Size data were presented based on the distribution by intensity.

Results

TABLE 1

Physicochemical characterization of ATRA loaded nanocarriers.

| Theoretical drug content (% w/w) | Drug | Average size (nm) | | PDI | | Zeta potential (mV) | |
|---|---|---|---|---|---|---|---|
| | | PLGA-np | PONC | PLGA-np | PONC | PLGA-np | PONC |
| blank | — | 175.0 ± 6.1 | 184.3 ± 1.8 | 0.06 ± 0.01 | 0.1 ± 0.02 | −12.7 ± 1.08 | −13.3 ± 1.12 |
| 1 | ATRA | 215.3 ± 2.8 | 217.4 ± 1.1 | 0.31 ± 0.11 | 0.10 ± 0.02 | −21.25 ± 0.28 | −18.45 ± 0.88 |
| 2 | ATRA | 214.9 ± 30 | 232.5 ± 6.2 | 0.34 ± 0.07 | 0.23 ± 0.02 | −13.76 ± 2.26 | −20.47 ± 3.6 |
| 3 | ATRA | 408.4 ± 111 | 217.3 ± 13.2 | 0.51 ± 0.15 | 0.24 ± 0.03 | −21.2 ± 2.49 | −14.02 ± 0.94 |
| 2 | IDMC | 188.8 ± 4.7 | 212.3 ± 15.1 | 0.09 ± 0.02 | 0.12 ± 0.02 | −17.43 ± 2.28 | −16.27 ± 0.32 |
| 3 | IDMC | 197.6 ± 2.6 | 213.7 ± 2.2 | 0.07 ± 0.01 | 0.11 ± 0.02 | −15.05 ± 3.03 | −19.31 ± 2.44 |

The data in Table 1 is represented as means±SD, sample N≥3. For ATRA loaded PONC, polymer to oil ratio was kept at 80:20 and for IDMC loaded PONC polymer to oil ratio was kept at 70:30.

As shown in Table 1, the size of the formulated nanospheres (Hybrid nanospheres ("PONC") including 20% oil and PLGA-np) was mostly found to be in the range of 175-232 nm. Overall, the hybrid nanospheres were moderately larger than PLGA-np except in the case of 3% ATRA loading where the PLGA-np were nearly twice as large as the hybrid nanospheres ($p<0.05$). In comparison, the differences between the polydispersity index (PDI) values of the two systems were noteworthy. The PDI of each hybrid nanosphere formulation was significantly lower than the PLGA-np of the same drug loading, which all had PDI values over 0.3 ($p<0.05$). The difference was especially substantial (PDI=0.51 vs 0.24) in the 3% drug loading group. The high PDIs of PLGA-np strongly indicated undesirable bimodal size distribution, which was likely caused by the presence of large unencapsulated drug aggregates.

The zeta potentials of unloaded and drug loaded hybrid nanospheres and PLGA-np were found to be negative (−15 mV to −20 mV, Table 1). The nanosphere polymer matrix in this study comprised ester end-capped polymer. Hence, the zeta potential is less negative compared to the non end-capped polymer reported in the earlier literature (Sirsi et al., 2009, Formulation of polylactide-co-glycolic acid nanospheres for encapsulation and sustained release of poly(ethylene imine)-poly(ethylene glycol) copolymers complexed to oligonucleotides. *J Nanobiotechnology* 7, 1).

Table 1 also summarizes the size and zeta potential values of nanocarriers loading the less lipophilic drug IDMC. Similar to ATRA-loaded formulations, IDMC-loaded hybrid nanospheres were moderately larger than the corresponding PLGA-np. The zeta potential was found to be in the same range as that of ATRA-loaded hybrid nanospheres i.e. between −15 to −20 mV. Oil inclusion in PLGA to form nanospheres did not significantly change the zeta potential.

Example 2. Measurement of Nanosphere Encapsulation Efficiencies

The following experiment demonstrates the substantial improvement of lipophilic drug encapsulation efficiency achieved by the hybrid nanospheres of the invention.
Measuring Encapsulation Efficiency (EE)

Each nanoparticle sample freshly prepared (as in Example 1) was centrifuged at 15,000 rpm at 16° C. for 25-30 minutes. The pellets of nanospheres were washed with copious distilled water. Washed nanospheres were dissolved in DMSO, and the amount of drug entrapped was analyzed spectrophotometrically using Spectramax M2 microplate reader (Molecular Devices, Sunnyvale, Calif.) at 360 nm for ATRA and 290 nm for IDMC. The linear calibration curve for ATRA was obtained in DMSO in the range of 1.25 µg/ml to 20 µg/ml ($r^2$=0.999). Blank, drug-free nanospheres served as the background control and we did not detect significant absorbance at the selected wavelengths. Experiments were repeated in triplicates.

Encapsulation efficiency (EE) was calculated by the following formula:

EE (%)=(Amount of drug encapsulated/Amount of drug added)×100%

Results

FIG. 2 compares the EE values of hybrid nanospheres of the invention and PLGA-np loading ATRA or IDMC. In general, the EE values of the hybrid nanospheres were substantially higher than that of their corresponding PLGA-np formulations in all groups (p<0.05). For loading of 1%, 2% and 3% (w/w) of ATRA, the EE values were increased by 135%, 259% and 202%, respectively (FIG. 2A). For loading of 2% and 3% IDMC, the EE values were increased by 124% and 74%, respectively (FIG. 2B). In terms of the absolute values of EE, there was a tendency to decline at higher loading of ATRA for both hybrid nanospheres and PLGA-np, whereas the changes were marginal for the IDMC formulations. This was expected given the extreme solubility behaviour of ATRA, which tended to precipitate out at higher concentrations even when already dissolved in the organic phase. Regardless, the hybrid nanospheres of the invention remained more efficient carriers than the standard PLGA-np for different drugs at different amounts of loading tested.

Figure 3A:
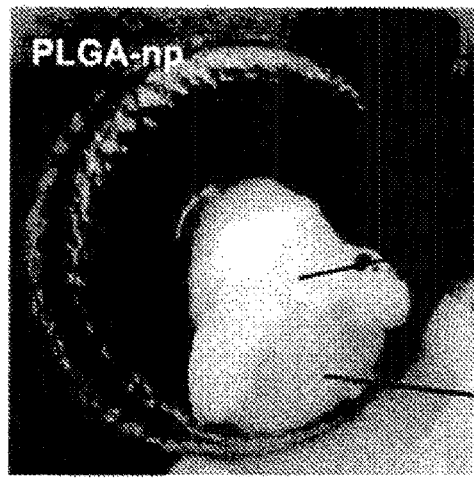
FIG. 3A is a photographic view of a centrifuge tube after centrifugation of PLGA-np at 15,000 rpm. A yellowish green fraction and a nearly colourless fraction are labeled in the figure, shown in greyscale
Figure 3B:
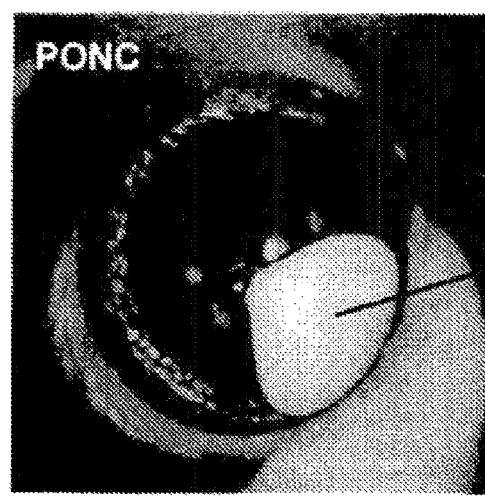
FIG. 3B is a similar photography of PONC nanospheres. A dark background was used for better visualization. The pellets of the PONC nanospheres remained homogeneous.

It should be pointed out that during the EE study, we noticed that after the centrifugation step, the pellets of the ATRA loaded PLGA-np tended to segregate into two visibly distinguishable fractions (a yellowish green fraction and a nearly colourless fraction are labeled in FIG. 3A, shown in greyscale), whereas the pellets of the hybrid nanospheres remained homogeneous (FIG. 3B). As ATRA is yellowish green in color, it was obvious that significant quantities of ATRA were never encapsulated in PLGA-np and simply precipitated out. Even though this unencapsulated drug was washed away with copious amounts of water, due to its poor water solubility, it was technically impossible to eliminate all the residual ATRA without over-handling the nanospheres. Hence, the above reported EE values of ATRA loaded PLGA-np are likely higher than they actually should be.

Example 3. Differential Scanning Calorimetry of Nanospheres

Differential Scanning Calorimetry (DSC) Measurements

Figure 4:
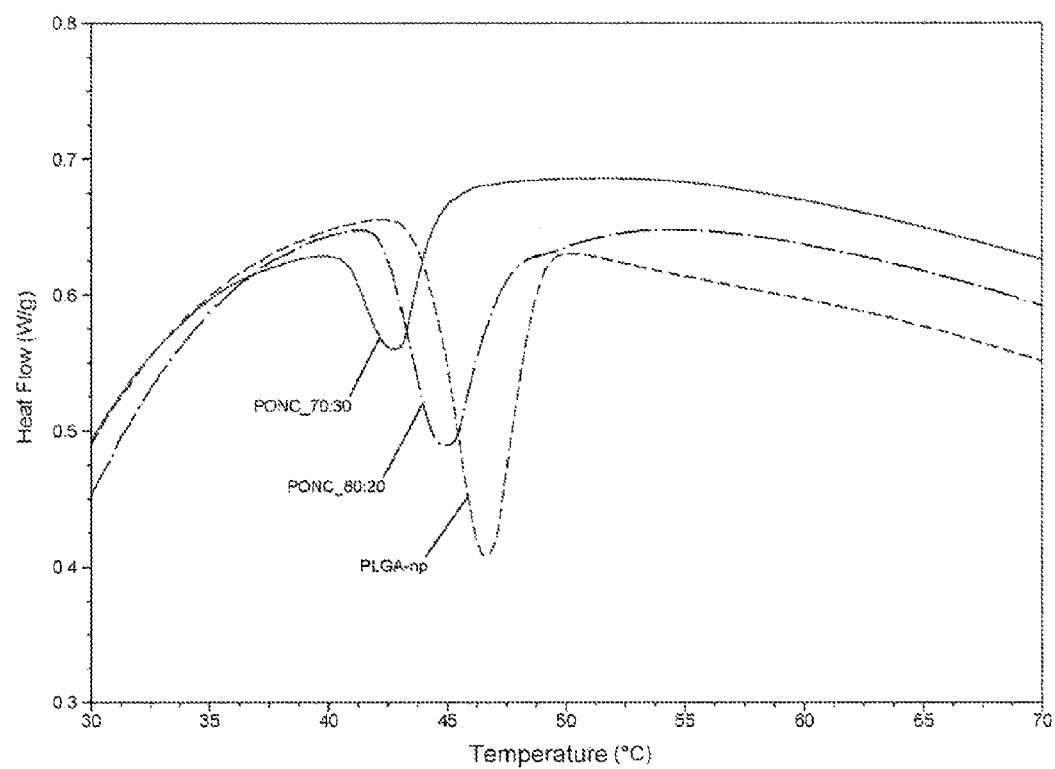
FIG. 4 illustrates a differential scanning calorimetry (DSC) thermogram of 1% ATRA-loaded (i) PLGA-np, (ii) PONC nanospheres (80/20, having 80% polymer and 20% oil), and (iii) PONC nanospheres (70/30, having 70% polymer and 30% oil) (percentage weights).

DSC analysis was carried out to evaluate the effect of oil inclusion on the degree of amorphosity of a PLGA matrix. Samples each containing 2-3 mg lyophilized nanospheres were weighted in aluminum pans, sealed, and equilibrated at 20° C. for 10 min. Analysis was performed using a DSC Q200 differential scanning calorimeter (TA Instruments, New Castle, Del.) at a heating rate of 10° C./min from 20 to 200° C. Data were collected and analyzed using software TA Universal Analysis 2000 (version 4.4A). DSC thermograms of nanospheres containing different quantity of oil (0-30%) were compared.
Results The thermal transition of polymer in the presence of the drug is shown in FIG. 4. The glass transition temperature of raw PLGA polymer (PLGA-np) was found to be 47.15° C. After incorporation of 20 and 30% of oil (with respect to polymer matrix), the glass transition temperature was reduced to 44.81 and 42.97° C. (FIG. 4: PONC 70:30; PONC 80:20). Analysis of the thermograms showed that the heat flow of PLGA-np was 4.1 J/g. This was reduced to 3.5 J/g after incorporation of 20% oil. Further increase in oil reduced the heat flow to 1.32 J/g. Our thermal analysis data demonstrate that with inclusion of oil in the polymer matrix, less energy was required for its thermal transition. This indicates an increase in amorphosity in the nanospheres.

Example 4. Nanosphere Release Kinetics

The following study demonstrates that the hybrid nanospheres of the invention display suppressed drug burst release and more even drug release than solid polymer nanospheres.
Drug Release Studies The amount of drug released in the medium was analyzed indirectly by determining the residual drug content in the nanospheres. For the drug release study, the nanospheres (prepared as in Example 1) were separated as described in the earlier section. The drug release studies were carried out in PBS (pH 7.4) at 37° C. The required amount of nanospheres was redispersed with the help of slight sonication in 1 ml of PBS and then transferred to cellulose ester dialysis bags (MWCO=10 KD) that had been washed with distilled water and pre-conditioned by equilibrating with the dissolution medium for 30-40 minutes. The sealed bags were placed in 1 L PBS medium at 37° C. under magnetic stirring at 120 rpm. At each time interval, the content of a bag was taken out and the residual drug content in the nanospheres were spectrophotometrically determined as described in above in the section on drug encapsulation efficiency. All the experiments were repeated in triplicate.

Results

Figure 5A:
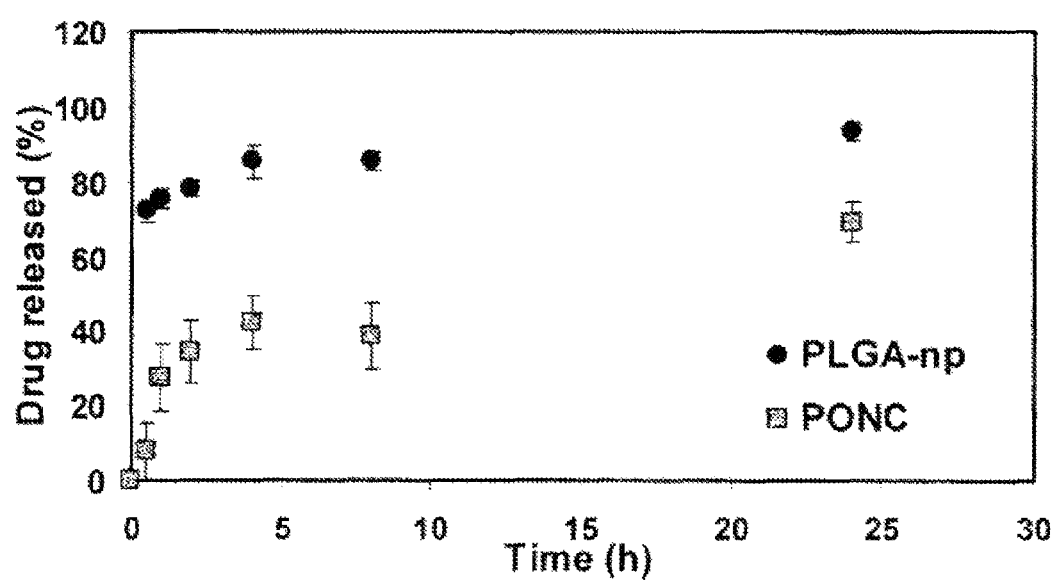
FIG. 5A is a plot of the in vitro drug release profiles of 1% w/w ATRA-loaded (i) PLGA-np and (ii) PONC nanospheres in phosphate-buffered (PBS) at 37° C. All the experiments were repeated in triplicate.

FIGS. 5A and 5B compare the ATRA release profiles of the hybrid nanospheres (PONC) and PLGA-np. To ensure fair comparison by avoiding excessive residual unencapsulated drug in the PLGA-np samples, the lower drug loading nanospheres (1% ATRA) were used for the study. The initial burst release effect of the nanospheres was significantly reduced compared to the PLGA-np (p<0.05), FIG. 5A. Within the first 30 minutes, 70% of drug was released in the case of PLGA-np while only 7.89% of drug was released from the nanospheres (FIG. 5B). After 24 h, 93.4% of drug was released from PLGA-np while around 69% drug release was observed from the nanospheres. The more even release kinetics of the nanospheres indicated better and more uniform encapsulation of ATRA by the polymer-oil matrix.

Example 5. Stability Study on Lyophilized Nanospheres

Stability studies were carried out on lyophilized samples of hybrid nanospheres loaded with 1% ATRA for 14 days at three different storage conditions.

Stability Studies

Nanospheres prepared as in Example 1 were resuspended in 1 ml of DI water and lyophilized for 48-72 h. The lyophilized samples were stored in the glass vials at either room temperature, 4° C. or −20° C. for 14 days. At preselected time intervals, samples were withdrawn and the nanospheres were redispersed in distilled water with slight sonication for 10-15 seconds and characterized for size, zeta potential, and encapsulation efficiency. Furthermore, DSC thermal analysis was performed to study the effect of time and temperature on the thermal properties of the nanoparticle samples.

Results

Figure 6A:
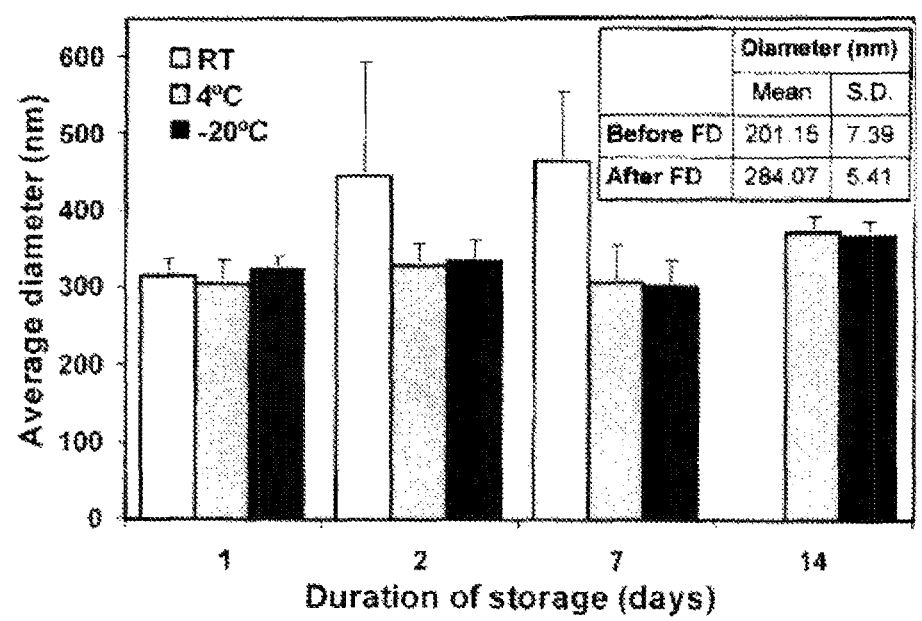
FIGS. 6A, 6B, 6C and 6D illustrate the effects of storage conditions on the various physicochemical properties of PONC nanospheres at room temperature (RT), 4° C. and −20° C.
Figure 6B:
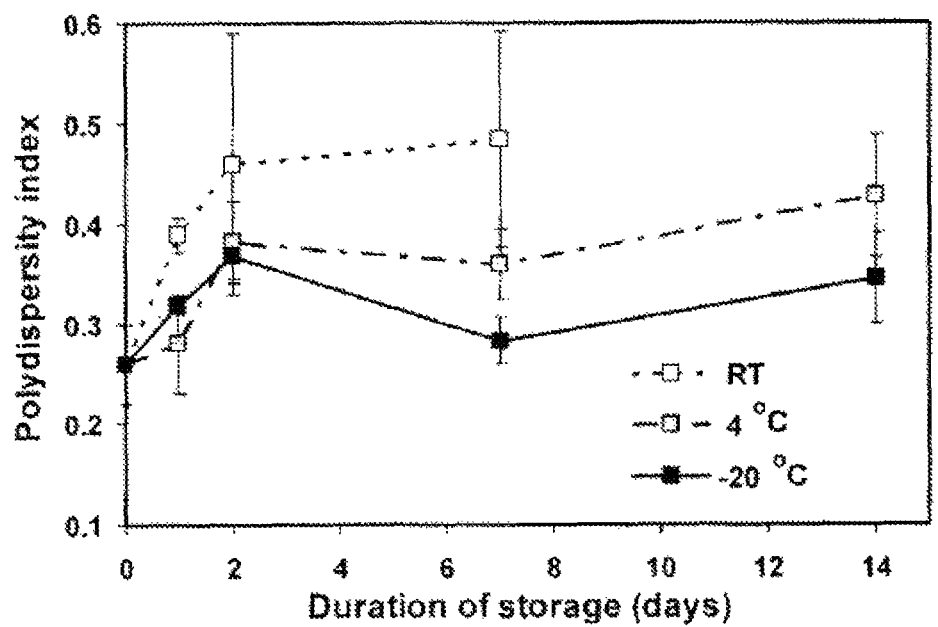
Figure 6C:
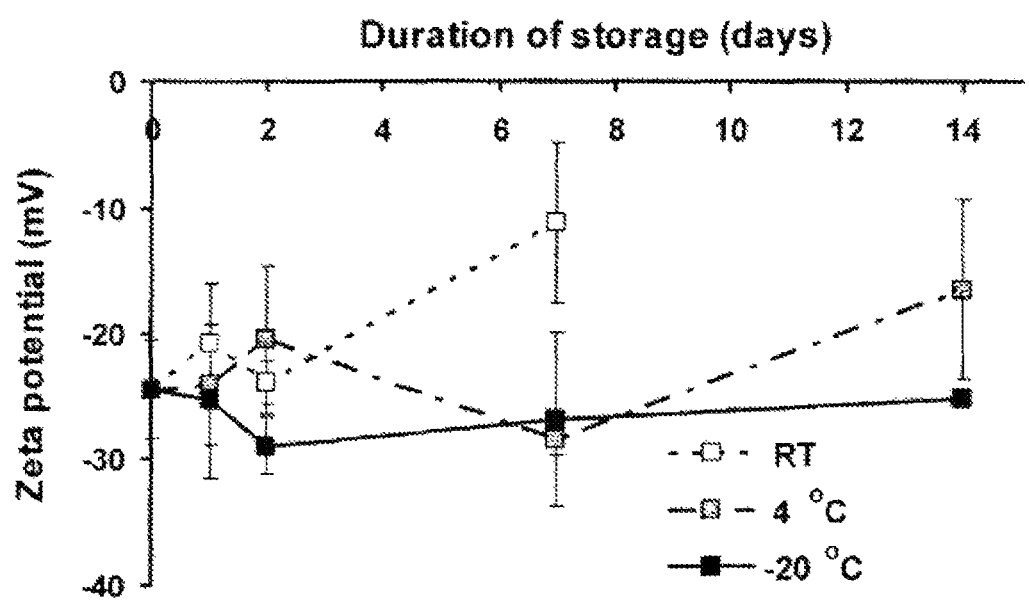
Figure 6D:
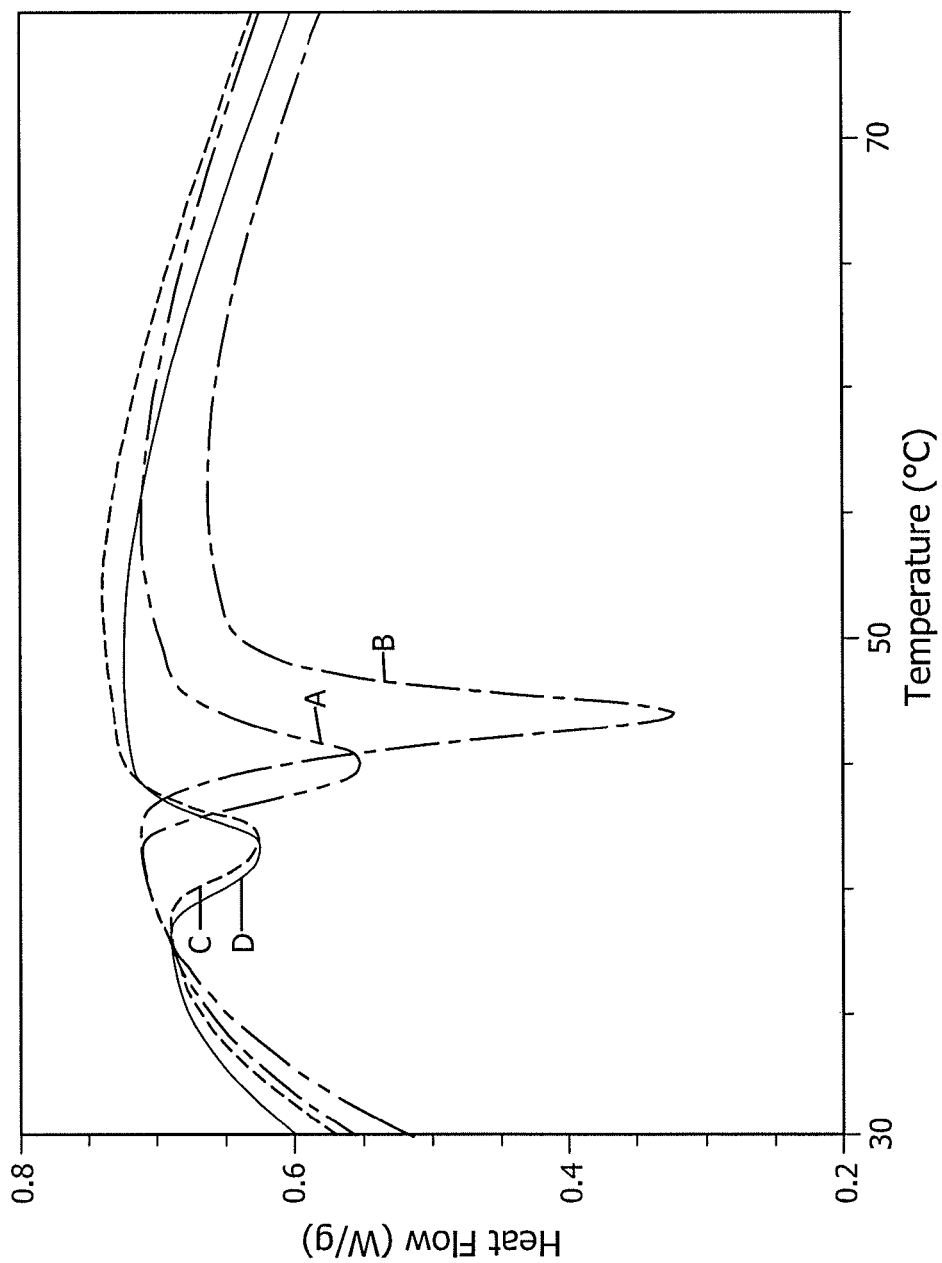

FIGS. 6A-6D summarize the results. As shown in the table in FIG. 6A, lyophilization of nanospheres resulted in a size increase from 201.15 nm to 284.07 nm likely caused by some degree of aggregation. The lyophilized sample was divided into three batches and stored at room temperature (RT), refrigerated (4° C.) or frozen (−20° C.). The RT group demonstrated considerable increase in particle size (from 284.07±5.41 nm after 1 day to 465.60±89.65 nm after 7 days). This was associated with significant increase in PDI from less than 0.3 to close to 0.5 (FIG. 6B) and diminishing zeta potential from about −25 mV to close to −10 mV (FIG. 6C). After 7 days we decided that the RT samples had too much aggregation and were not suitable for measurements on day 14.

By comparison, the 4° C. and −20° C. groups were quite stable. Moderate increases in size after 14-day storage were observed (FIG. 6A). The −20° C. group was especially stable. The average PDI value increased only from 0.32 on day 1 to 0.35 after 14 days of storage (FIG. 6B). This was associated with no significant change in its zeta potential value (FIG. 6C).

DSC studies were performed to evaluate the storage effect on the thermal properties of the nanospheres. The DSC thermograms (FIG. 6D) were recorded before storage and on the last day of their storage ($7^{th}$ day for RT, $14^{th}$ day for 4° C. or −20° C.). It is clear that the Tg peak of the RT group became significantly more intense compared to the other two groups. Interestingly, the two low temperature groups actually required less energy for the phase transition and had lower Tg when compared to the sample before storage.

Example 6. Intrinsic Carrier Toxicity of the Hybrid Nanospheres is Comparable to Standard PLGA Nanoparticles MTT assays were performed as follows to evaluate the intrinsic carrier toxicity of PLGA nanospheres in human prostate RWPE-1 and PC-3 cell lines. Particular emphasis was placed on the cell-type non-specific toxicity. For this purpose two different types of cells were used, i.e. non-cancerous human prostate cell lines (RWPE-1) and cancerous human prostate cell line (PC-3).

Toxicity Studies

Subconfluent cells were seeded in 96-well microplate and allowed to attach under standard cell culture conditions. After 24 h, blank nanospheres and PLGA-np (0.05% to 5% w/v) prepared according to Example 1 were added to the microplate wells and incubated for 48 h at 37° C. After 48 h, 20 µl of 5 mg/ml 3-(4,5-dimethylthiazol-2-yl)-2,5-diphenyltetrazolium bromide (MTT) reagent was added to the wells and allowed to incubate for 2 h. At the end of the 2 h, the medium was discarded. To each well, 100 µl of DMSO was added to dissolve the purple formazan dye produced by the metabolically active cells. The UV absorbance of the colored dye produced was measured at 560 nm. Untreated cells were used as control.

Results

Figure 7A:
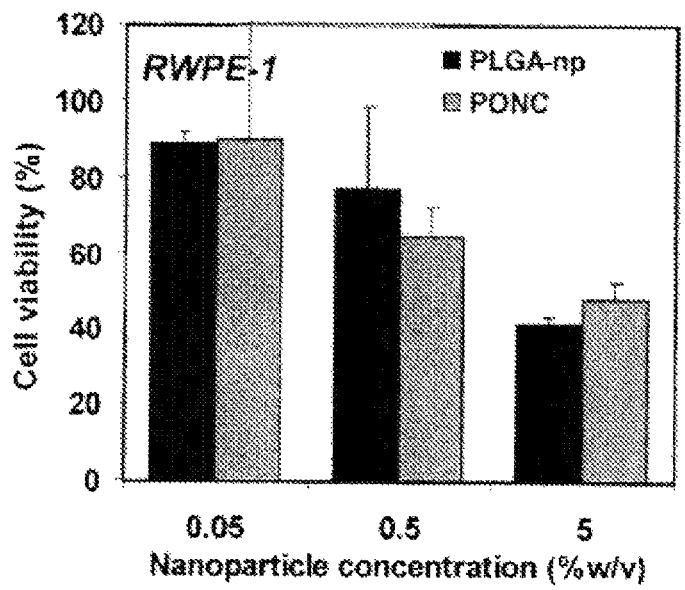
FIG. 7A illustrates the results of (3-(4,5-dimethylthiazol-2-yl)-5-(3-carboxymethoxyphenyl)-2-(4-sulfophenyl)-2H-tetrazolium) (MTT) assays to evaluate the toxicity of blank PLGA-np and blank PONC nanospheres on RWPE-1 human prostate epithelial cells.
Figure 7B:
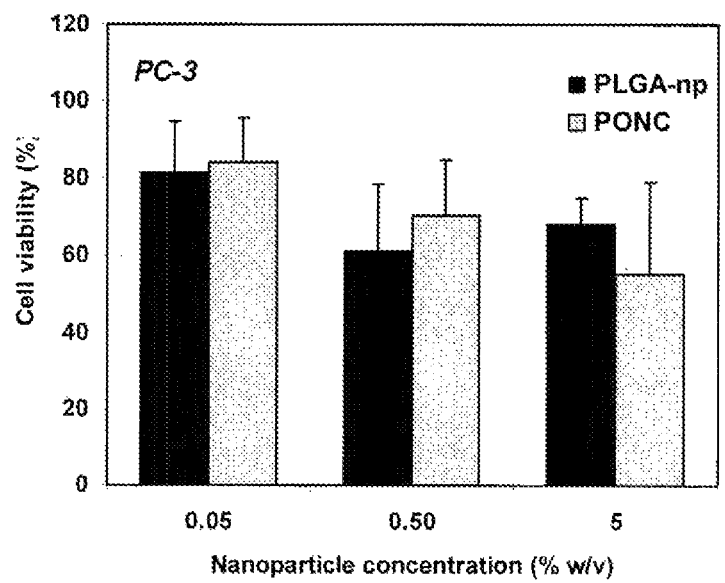
FIG. 7B illustrates the results of MTT assays to evaluate the toxicity of blank PLGA-np and blank PONC nanospheres on human prostate cancer PC-3 cells.

The results are shown in FIGS. 7A and 7B (RWPE-1, FIG. 7A and PC-3, FIG. 7B). The results show that the intrinsic carrier toxicity of the hybrid nanospheres is comparable to that of standard PLGA nanoparticles.

Figure 7C:
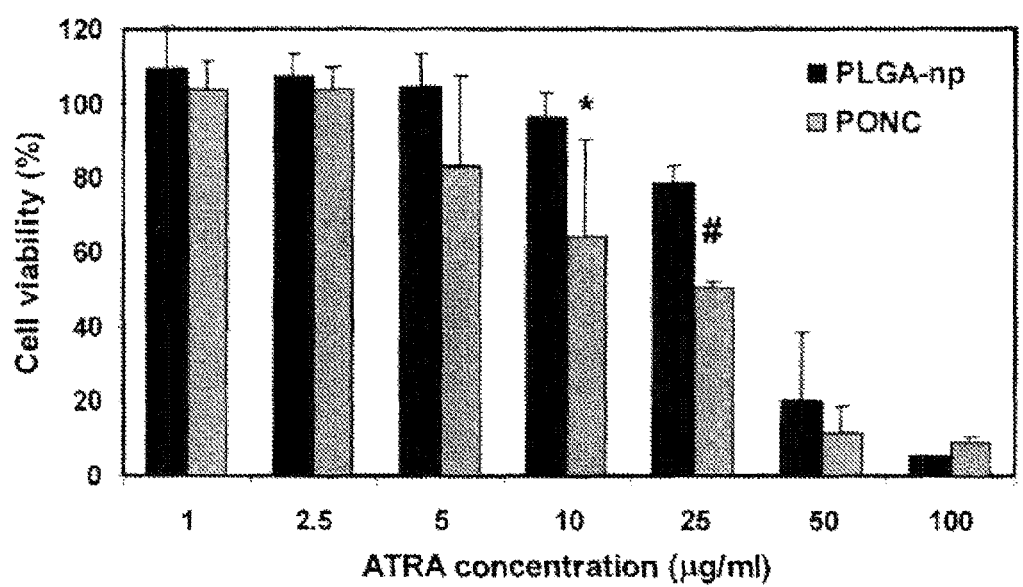
FIG. 7C illustrates MTT assays to evaluate the anticancer activity of ATRA-loaded PONC nanospheres and PLGA-np on PC-3 cells. In both studies cells were treated for 48 h before assays were performed. Results are presented as means±S.D. (N≥3). * p<0.05, # p<0.001.

Example 7. Nanospheres Improved the Anti-Cancer Activity of ATRA Over PLGA Nanoparticles As ATRA by itself is an anticancer agent, we further compared the anticancer activities of ATRA-loaded hybrid nanospheres and ATRA-loaded PLGA-np, adjusted for ATRA concentrations. The same conditions were employed as for the above MTT assays on blank particles in Example 6. Unexpectedly, ATRA-loaded nanospheres demonstrated moderate but clearly significant anticancer activity on PC-3 cells when compared to the standard PLGA-np formulation at medium concentrations (FIG. 7C).

In hybrid nanospheres, ATRA is already in a highly dispersed, already solubilized form that can be readily usable by the cancer cells, and therefore the drug can actually be more efficiently delivered and utilized.

Example 8. Pegylation of Nanospheres Improved the Delivery of Lipophilic Compounds PONC were surface-functionalized with polyethylene glycol 2000. The pegylated PONC (PEG-PONC) were prepared by the emulsion-solvent evaporation technique using ingredients as listed in Table 2. ATRA was dissolved in oil (Captex 200) by incubating at room temperature overnight, and the resulting drug-oil phase was diluted with 1 ml dichloromethane. To this solution the mixture of PLGA and PEG-PLGA co-polymers were dispersed. Depending on the required degree of pegylation the amount of PEG-PLGA polymer and PLGA was adjusted. The resulting organic phase was added dropwise to 5 ml 1.5% w/v aqueous solution of polyvinyl alcohol (PVA) over a period of 2 min under constant stirring. The mixture was vortexed for 10-15 seconds and subjected to sonication for 6 min on ice (40 kHz, 120V, Bransonic 3510, Danbury, Conn.). The emulsion formed was stirred overnight for solvent evaporation. The nanocarriers formed were freshly used or lyophilized for experiments. The same procedure was used for the preparation of standard PEG-PLGA only nanoparticles (i.e. PEG-PLGA-np) with exclusion of oil.

TABLE 2

List of ingredients for making PEG-PONC.

| Initial ATRA loading (% w/w) | Drug (mg) | Polymer PLGA (mg) | Polymer peg-PLGA | Oil (mg) | PVA (% w/v) | DCM (ml) | Water (ml) |
|---|---|---|---|---|---|---|---|
| 1 | 0.3 | 21.6 | 2.4 | 6 | 1.5 | 1 | 5 |
| 5 | 1.5 | 21.6 | 2.4 | 6 | 1.5 | 1 | 5 |
| 10 | 3.0 | 21.6 | 2.4 | 6 | 1.5 | 1 | 5 |

Figure 8:
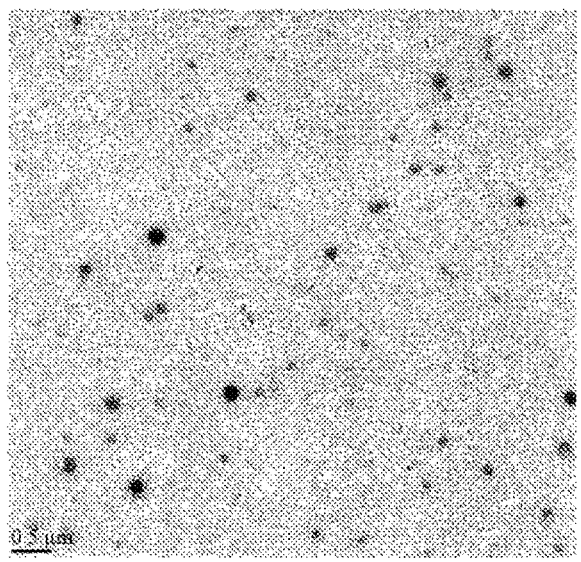
FIG. 8 illustrates a transmission electron microscope (TEM) image of a PONC surface functionalized with polyethylene glycol 2000. Nanospheres contain 5% w/w all-trans retinoic acid. Scale bar indicates 5 μm.

The morphology of nanoparticles was determined by transmission electron microscope using JEOL, JEM-1400 TEM (Tokyo, Japan) at 120 kV. A drop of nanoparticle suspension (concentration: 0.5 mg/ml) was placed on a 400 mesh copper grid (Ultra thin carbon type A, Ted Pella Inc., Redding, Calif.). Samples were air-dried in the hood before examination. A transmission electron microscope (TEM) image of the pegylated nanospheres is shown in FIG. 8.

Figure 9:
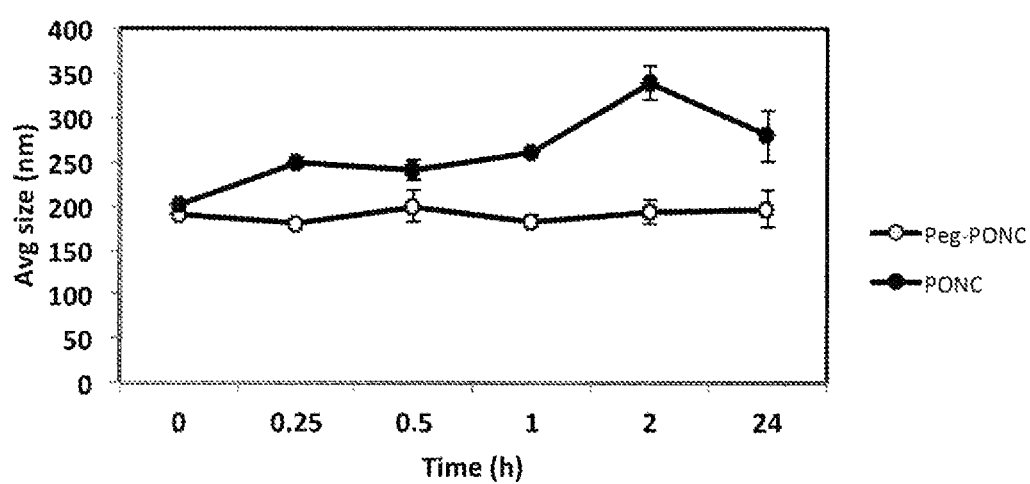
FIG. 9 illustrates the effect of serum on the stability of nanospheres. Non-functionalized polymer-oil nanocarrier (PONC) and PONC surface-functionalized with polyethylene glycol 2000 (PEG-PONC) were incubated with 10% bovine serum albumin at 37° C. in phosphate buffered saline (pH 7.4), and the size of the nanospheres was monitored with photon correlation spectroscopy.

The effect of serum on the stability of nanospheres was evaluated. Non-functionalized PONC and PONC surface-functionalized with polyethylene glycol 2000 (PEG-PONC) were incubated at a concentration of 3 mg/ml with 10% bovine serum albumin at 37° C. in phosphate buffered saline (pH 7.4) and the size of the nanospheres was monitored with photon correlation spectroscopy as shown in FIG. 9.

The ability of PEG-PONC to improve delivery of lipophilic compounds to drug-resistant cancer cells was evaluated. The PEG-PONC nanospheres were prepared as described above. The nanoparticles were loaded with 1% w/v nile red dye. For evaluation of nanoparticle uptake into the cells, skov-3$_{PR}$ human ovarian cancer cells were grown in RPMI-1640 medium supplemented with 300 nM paclitaxel, 10% fetal bovine serum, 100 IU/ml penicillin G and 100 µg/ml streptomycin in 35-mm culture dishes each containing a poly-L-lysine coated no. 1 cover glass, and treated with PEG-PONC delivering nile red for 4 and 24 h. As a control, a similar experiment was carried out with nile red dye that was not encapsulated within PEG-PONC, but rather was added as a dye solution together with blank PEG-PONC. The cells were viewed with an Axiostar Plus epifluorescence microscope (Carl Zeiss, Oberkochen, Germany) using Insight camera model 8.0 for image capture. Images were analyzed using Spots Advanced imaging software (v. 4.6, Diagnostic Instrument, Sterling Heights, Mich.).

The results showed that by carrying the dye within the PEG-PONC nanospheres a substantial improvement in dye delivery into the cancer cells could be achieved, compared to the delivery of dye that was not encapsulated in PEG-PONC nanospheres (data not shown). This indicates that PEG-PONC nanospheres may be used in the delivery of drug into drug-resistant cancer cells.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

The invention claimed is:

1. A nanosphere for delivery of a therapeutic agent comprising:
    a polymer matrix;
    discrete liquid oil droplets dispersed in the polymer matrix; and
    a therapeutic agent dissolved or dispersed in the oil droplets.

2. The nanosphere of claim 1 wherein said nanosphere is pegylated.

3. The nanosphere of claim 1 wherein said nanosphere has a diameter of from about 100 nm to about 300 nm.

4. The nanosphere of claim 1 wherein said oil comprises a lipid or a phospholipid.

5. The nanosphere of claim 1 wherein said oil is selected from the group consisting of palmitoleic acid, oleic acid, linoleic acid, α-linoleic acid, arachidonic acid, propylene glycol monocaprylate, propylene glycol dicaprylate, propylene glycol dicaprate, glycerol monocaprate and glycerol monooleate.

6. The nanosphere of claim 4 wherein said lipid or said phospholipid has a melting point below 20° C.

7. The nanosphere of claim 1 wherein said polymer is a natural, modified or synthetic polymer.

8. The nanosphere of claim 1 wherein said polymer is biodegradable.

9. The nanosphere of claim 1 wherein said polymer is selected from the group consisting of a polylactic acid polymer, a polyglycolic acid polymer, a poly(lactic-co-glycolic acid) copolymer, an acrylic polymer, a polyhydroxyalkanoate polymer, a polyethylenimine polymer, an acrylamide polymer and a chitosan polymer.

10. The nanosphere of claim 1 wherein said therapeutic agent is a poorly water soluble drug.

11. The nanosphere of claim 10 wherein said poorly water soluble drug is an antineoplastic agent, a steroidal hormone, a sex hormone, an anti-fungal drug, an anti-viral drug, an antibiotic, an opioid agonist, an opioid antagonist, a calcium channel blocker, an antiangiogenic drug, a diagnostic compound, a vitamin or a cosmetic compound.

12. The nanosphere of claim 1 wherein said therapeutic agent is interferon, macrophage activation factor, an interleukin, colony stimulating factor, tumor degenerating factor, epidermal growth factor, erythropoietin, tissue plasminogen activator, insulin, luteinizing hormone releasing hormone, an enzyme, a vaccine or an antibody.

13. The nanosphere of claim 12 wherein said enzyme is urokinase or superoxide dismutase.

14. The nanosphere of claim 1 wherein said nanosphere is prepared by emulsion-solvent evaporation of a solvent for said polymer.

15. A method for preparing a nanosphere according to claim 1 comprising the steps of:
    dissolving or dispersing a therapeutic agent in an oil;
    adding a solvent for the therapeutic agent and the oil to form a solution;
    adding a polymer to said solution with mixing to form a mixture;
    adding said mixture to a solvent for the polymer with mixing; and
    evaporating the solvent for the polymer to obtain a nanosphere comprising said therapeutic agent dissolved or dispersed in discrete liquid oil droplets dispersed in a matrix formed by said polymer.

16. The method of claim 15 wherein said solvent for the polymer is an alcohol.

17. The method of claim 15 wherein said nanosphere has a diameter of from about 100 nm to about 300 nm.

18. The method of claim 15 wherein said oil comprises a lipid or a phospholipid.

19. The method of claim 18 wherein said lipid or said phospholipid has a melting point below 20° C.

20. The method of claim 15 wherein said polymer comprises a natural, modified or synthetic polymer.

21. The method of claim 15 wherein said polymer is biodegradable.

22. The method of claim 15 wherein said therapeutic agent is a poorly water soluble drug.

23. The method of claim 22 wherein said poorly water soluble drug is an antineoplastic agent, a steroidal hormone, a sex hormone, an anti-fungal drug, an anti-viral drug, an antibiotic, an opioid agonist, an opioid antagonist, a calcium channel blocker, an antiangiogenic drug, a diagnostic compound, a vitamin or a cosmetic compound.

24. The method of claim 15 wherein said therapeutic agent is interferon, macrophage activation factor, an interleukin, colony stimulating factor, tumor degenerating factor, epidermal growth factor, erythropoietin, tissue plasminogen activator, insulin, luteinizing hormone releasing hormone, an enzyme, a vaccine or an antibody.

25. The method of claim 24 wherein said enzyme is urokinase or superoxide dismutase.

26. The nanosphere of claim 1 wherein the glass transition temperature of the nanosphere is lower than that of the polymer matrix alone.

27. The nanosphere of claim 1 wherein said nanosphere is amorphous.

28. The method of claim 15 wherein the glass transition temperature of the nanosphere is lower than that of the polymer matrix alone.

29. The method of claim 15 wherein said nanosphere is amorphous.

* * * * *